(12) United States Patent
Chang et al.

(10) Patent No.: US 11,730,816 B2
(45) Date of Patent: Aug. 22, 2023

(54) DEBRANCHING ENZYME MODIFIED STARCH, THE PREPARING METHOD AND USE THEREOF IN HARD CAPSULE PRODUCTION

(71) Applicant: DAH FENG CAPSULE INDUSTRY CO., LTD., Taichung (TW)

(72) Inventors: Ruei-Jan Chang, Taichung (TW); Hsin-Yi Chao, Taichung (TW); Pei-Hsuan Lee, Taichung (TW); Wei-Yu Chen, Taichung (TW)

(73) Assignee: DAH FENG CAPSULE INDUSTRY CO., LTD, Taichung (TW)

( * ) Notice: Subject to any disclaimer, the term of this patent is extended or adjusted under 35 U.S.C. 154(b) by 193 days.

(21) Appl. No.: 17/328,329

(22) Filed: May 24, 2021

(65) Prior Publication Data

US 2021/0275675 A1 Sep. 9, 2021

Related U.S. Application Data

(62) Division of application No. 16/122,288, filed on Sep. 5, 2018, now abandoned.

(30) Foreign Application Priority Data

Jul. 19, 2018 (TW) ................. 107124942

(51) Int. Cl.
  *A61K 47/36* (2006.01)
  *A23L 29/219* (2016.01)
  *A61K 9/48* (2006.01)

(52) U.S. Cl.
  CPC ............ *A61K 47/36* (2013.01); *A23L 29/219* (2016.08); *A61K 9/4816* (2013.01); *A23V 2002/00* (2013.01)

(58) Field of Classification Search
  None
  See application file for complete search history.

(56) References Cited

U.S. PATENT DOCUMENTS

| 4,971,723 A | 11/1990 | Chiu |
| 8,703,465 B2 | 4/2014 | Borchert et al. |

FOREIGN PATENT DOCUMENTS

| CN | 102525995 B | 10/2013 | |
| CN | 103830736 B | 1/2015 | |
| WO | WO-2003035045 A2 | 5/2003 | |
| WO | WO-2012028702 A1 * | 3/2012 | .............. A61J 3/077 |

OTHER PUBLICATIONS

Liu, Guodong, et al. "Preparation and characterization of pullulanase debranched starches and their properties for drug controlled-release." RSC advances 5.117 (2015): 97066-97075. (Year: 2015).*
Palacios-Fonseca, A. J., et al. "Effect of the alkaline and acid treatments on the physicochemical properties of corn starch." CyTA-Journal of Food 11.sup1 (2013): 67-74. (Year: 2013).
Pongsawatmanit, Rungnaphar, et al. "Influence of tamarind seed xyloglucan on rheological properties and thermal stability of tapioca starch." Journal of Food Engineering 77.1 (2006): 41-50. (Year: 2006).

* cited by examiner

*Primary Examiner* — Robert J Yamasaki
(74) *Attorney, Agent, or Firm* — Muncy, Geissler, Olds & Lowe, P.C.

(57) ABSTRACT

The present invention relates to a modified starch and a method for obtaining the modified starch by using a debranching enzyme, such as isoamylase, pullulanase, limit dextrinase and the like. The debranching enzyme modified starch of present invention exhibits excellent film-forming capacity, film strength, and gelation ability, so as to be used as a material for making hard capsules without the use of coagulants and plasticizers.

4 Claims, No Drawings

DEBRANCHING ENZYME MODIFIED STARCH, THE PREPARING METHOD AND USE THEREOF IN HARD CAPSULE PRODUCTION

CROSS-REFERENCE TO RELATED APPLICATION

This application claims priority to Taiwan Patent Application No. 107124942, filed on Jul. 19, 2018, the entire content of which is hereby incorporated by reference herein in its entirety.

BACKGROUND OF THE INVENTION

Technical Field of the Invention

The present invention relates to a modified starch obtained by utilizing a debranching enzyme and a preparation method thereof. More particularly, it relates to a use of debranching enzyme modified starch for manufacturing of hard empty capsules, and a preparation method thereof.

Background

Starch is a natural material that is inexpensive and widely sourced, and its safety has been verified for a long time. However, capsules made from natural starch or chemically modified starch often have disadvantages such as high viscosity of the gel and insufficient strength (fragileness), thus limiting the application of starch in hard empty capsules and other packaging materials.

There have been prior art attempts to treat starch by enzymes, with the intention of applying the modified starch gel obtained to the manufacture of empty capsules. For instance, Chinese patent CN 102525995B discloses a preparation method of a medicinal plant empty capsule, which comprises a partially isoamylase hydrolyzed kudzu powder, an enhancer, a gelatinizing agent, a plasticizer, a coagulant, a dispersant and food coloring etc. After mixing and demolding, the formed medicinal plant empty capsules are obtained.

Chinese patent CN103830736B discloses a method for producing a starch empty capsule, which primarily utilizes a low-viscosity starch gel obtained by reacting starch with a coagulant, a plasticizer and an enzyme selected from α-amylase, β-amylase, γ-amylase or isoamylase as a raw material. Although the two prior arts mentioned that the starch could be modified by isoamylase to be used in the manufacture of empty capsules, it is not explicitly disclosed that the modified starch with lower degree of branching and excellent gelation ability can be obtained by the utilization of debranching enzyme.

Therefore, the present invention attempts to reduce the degree of branching of the starch by using the debranching enzyme, so that the modified starch possesses excellent gelation ability, film-forming capacity and film strength, and can be applied to the manufacture of hard empty capsules for use in food- and medical related fields.

SUMMARY OF INVENTION

Based on the above object, the present invention demonstrates that by treating a starch with a debranching enzyme (for example, isoamylase and pullulanase), a modified starch exhibits excellent film-forming capacity and material strength can be obtained, that is, the starch modified by the debranching enzyme possesses properties suitable for making a hard empty capsule.

Accordingly, one aspect of the invention relates to a modified starch gel for manufacturing of hard empty capsules, which characterized in that the modified starch is obtained by reacting a starch solution with a debranching enzyme, and possesses gelation ability and enhanced film strength.

In some embodiments of the present invention, the starch include, but is not limited to, native starch and chemically modified starch. The natural starch includes any starch present in natural grains or legumes such as, but not limited to, corn starch, potato starch, tapioca starch, wheat starch, pea starch, mung bean starch, and so on. The chemically modified starch includes any starch obtained by modifying a natural starch by physical and chemical processes and introducing an ester or ether functional group to change the original physical property of the natural starch, such as but not limited to, waxy starch, hydroxypropyl starch, oxidized starch, carboxymethyl starch, esterified starch and so on.

In other embodiments of the present invention, the starch debranching enzyme includes, but is not limited to, isoamylase, pullulanase, limit dextrinase and so on.

Another aspect of the present invention relates to a method for preparing a modified starch gel, characterized in that it comprises: fully dissolving starch in water (1:4-1:5 wt/wt); adding starch debranching enzyme (the amount of enzyme is 0.00001% to 5% the weight of the starch), and reacting at 40-60° C. for 2-3 hours; heating to 85° C. or above to inactivate the enzyme; and cooling to 40-60° C. to obtain a modified starch gel.

In some embodiments of the present invention, the starch debranching enzyme includes, but is not limited to, an isoamylase, a pullulanase, a limit dextrinase, and so on. In one embodiment of the present invention, the starch debranching enzyme is an isoamylase. In another embodiment of the invention, the starch debranching enzyme is a pullulanase.

A further aspect of the present invention relates to a preparation method of hard empty capsules, including steps of: dissolving a starch in water at a weight ratio of about 1:2 to 1:10 to obtain a starch solution at 85° C.; adding a debranching enzyme to the starch solution to obtain a mixture, wherein the amount of the debranching enzyme is 0.00001% to 5% of the weight of the starch, and reacting the mixture at 40-70° C. for 0.5-5 hours; heating the mixture to 80° C. or above to inactivate the debranching enzyme; cooling the mixture to 40-70° C. to obtain a modified starch gel, wherein the modified starch gel is without coagulants and plasticizers and has a degree of branching that is reduced by 30% to 100% and a viscosity of 2,000 to 5,000 cps measured at a gel temperature of 60° C.; and using the modified starch gel as a raw material to form a shell of the hard empty capsule.

BRIEF DESCRIPTION OF THE DRAWINGS

None

DETAILED DESCRIPTION OF THE INVENTION

As used herein, "starch debranching enzyme" or "debranching enzyme" refers to the enzyme specifically cleaves the α-1,6 glucosidic linkage in the starch structure, lowering the degree of branching of the starch treated. The starch debranching enzyme used in the present invention may include, but is not limited to, an isoamylase, a pullulanase, a limit dextrinase, and so on.

The "debranching enzyme modified starch" of the present invention having a degree of branching reduced by about 30%-100%, and possesses a markedly reduced viscosity and excellent gelation ability. Therefore, in the production of capsules and other applications, the addition of a gelatinizing agent and an auxiliary for gelation is not necessary.

Other features and advantages of the present invention will be further exemplified and described in the following examples, which are intended to be illustrative only and not to limit the scope of the invention.

Example 1: Preparation of Isoamylase Modified Starch Gel 100 grams of starch was fully dissolved in 500 grams of pure water at 85° C. The starch solution was cooled to 40-60° C., and 0.1 U to 20,000 U of isoamylase was added, and the reaction was conducted for 2 hours. The reaction mixture is heated to a high temperature (above 85° C.) to inactivate the enzyme and quench the reaction. The reaction mixture was cooled to 40-60° C. again, and the modified starch gel (1) was obtained.

Example 2: Preparation of Pullulanase Modified Starch Gel 100 grams of starch was fully dissolved in 500 grams of pure water at 85° C. The starch solution was cooled to 40-600° C., and 0.1 U to 20,000 U of pullulanase was added, and the reaction was conducted for 2 hours. The reaction mixture is heated to a high temperature (above 85° C.) to inactivate the enzyme and quench the reaction. The reaction mixture was cooled to 40-60° C. again, and the modified starch gel (2) was obtained.

Example 3: Preparation of Pullulanase Modified Starch Gel 100 grams of starch was fully dissolved in 500 grams of pure water at 85° C. The starch solution was cooled to 40-60° C., and 0.1 U to 20,000 U of pullulanase was added, and the reaction was conducted for 2 hours. The reaction mixture is heated to a high temperature (above 85° C.) to inactivate the enzyme and quench the reaction. The reaction mixture was cooled to 40-60° C. again, followed by adding 0.05%~5% of carrageenan and 0.01%~5% of potassium chloride, and the modified starch gel (3) was obtained.

Example 4: The Evaluation of Viscosity and Gelation Ability of Modified Starch Gel This viscosity measurement was conducted by utilizing a viscometer (Brookfield VTE250 1/2RV) at the gel temperature of 60° C. In addition, a comparative starch gel (1) without enzyme treatment and a comparative starch gel (2) modified with α-amylase were also prepared for comparison.

The comparative example starch gel (1) is prepared as follows: 100 grams of starch was fully dissolved in 500 grams of pure water at 85° C., and then the solution is cooled to 40-60° C. to obtain the comparative example starch gel (1).

The comparative example starch gel (2) is prepared as follows: 100 grams of starch was fully dissolved in 500 grams of pure water at 85° C. The starch solution was then cooled to 40-60° C., and 0.1 U to 20,000 U of α-amylase was added, and the reaction was conducted for 2 hours. The reaction mixture is heated to a high temperature (above 85° C.) to inactivate the enzyme and quench the reaction. The reaction mixture was cooled to 40-60° C. again, and the comparative example starch gel (2) was obtained.

Table 1 below shows the comparison of the viscosity and fluidness of the modified starch gels (1), (2), and (3) of the present invention and the comparative starch gels (1) and (2).

TABLE 1

The comparison of the viscosity and fluidness of the modified starch gels of the present invention and the comparative starch gels. "○" represents good fluidity of the gel, suitable for capsule production, while "X" is the opposite.

|  | Solid content (%) | Viscosity (cps) | Fluidness |
| --- | --- | --- | --- |
| modified starch gel (1) | 15.00 | 1000-5000 | ○ |
| modified starch gel (2) | 15.00 | 1000-5000 | ○ |
| modified starch gel (3) | 15.00 | 1000-5000 | ○ |
| comparative example starch gel (1) | 15.00 | 2000-10000 | X |
| comparative example starch gel (2) | 15.00 | 500-2000 | ○ |

On the basis of above results, the comparative example starch gel (1) made from general starch (no enzyme treatment) has excessive viscosity and poor fluidity, and is not suitable as a material for hard capsules. However, the starch gel made from the modified starch treated by the debranching enzyme such as isoamylase and pullulanase has a markedly reduced viscosity and appropriate fluidity, and is suitable as a material for hard empty capsules.

The burst strength of the capsule prepared by the debranching enzyme modified starch gel of the present invention and the comparative starch gel was further evaluated. The procedure is as follows: the capsules prepared by various kinds of gels with a capsule mold, 50 samples each, were laid on an iron pan, and allowed to stand at 19 to 27° C. for 24 hours. After that, place the sample in a glass tube standing on a wooden board, align the bottom end of a cylindrical weight (20 g) with the marking (indicates a height of 20 cm) of the glass tube, and then freely drop it to the capsule to check whether the capsule is fractured by the weight. The number of capsules which fracture occurred was documented, and the results are shown in table 2 below.

TABLE 2

The burst strength of the capsule prepared by the debranching enzyme modified starch gel of the present invention and the comparative starch gel. "○" represents that the capsule shell tough and not brittle, while "X" is the opposite.

|  | Burst strength (The number of capsules which fracture occurred) |
| --- | --- |
| modified starch gel (1) | ○ (<5) |
| modified starch gel (2) | ○ (<5) |
| modified starch gel (3) | ○ (<5) |
| comparative example starch gel (1) | X (>10) |
| comparative example starch gel (2) | X (>10) |

The comparative example starch gel (2) made from starch treated by α-amylase has reduced viscosity and improved fluidity, however, as a result of table 2, the capsules prepared therefrom exhibit fragileness and poor film-forming capacity. In contrast, the modified starch gel obtained by treating the debranching enzyme of the present invention has low viscosity and good fluidity, and the capsules made thereof have excellent strength and toughness and are not easy to be brittle.

In summary, the present invention first discloses the modification of starch by treating a debranching enzyme (for instance, isoamylase and pullulanase), and it is experimentally confirmed that the modified starch gel with excellent film-forming capacity and desirable material strength is suitable for the production of hard empty capsules.

The invention claimed is:

1. A method for producing a hard empty capsule, comprising:
    dissolving a starch in water at a weight ratio of about 1:2 to 1:10 to obtain a starch solution at 85° C.;
    adding a debranching enzyme to the starch solution to obtain a mixture, wherein an amount of the debranching enzyme is 0.00001% to 5% of the weight of the starch, and reacting the mixture at 40-70° C. for 0.5-5 hours;
    heating the mixture to 80° C. or above to inactivate the debranching enzyme; and
    cooling the mixture to 40-70° C. to obtain a modified starch gel, wherein the modified starch gel is without coagulants and plasticizers and has a degree of branching that is reduced by 30% to 100% and a viscosity of 2,000 to 5,000 cps measured at a gel temperature of 60° C.; and
    using the modified starch gel as a raw material to form a shell of the hard empty capsule.

2. The method of claim 1, wherein the mixture of the debranching enzyme and the starch is reacted at 40-60° C. for 2-3 hours.

3. The method of claim 1, wherein the starch is selected from the group consisting of natural starch and chemically modified starch.

4. The method of claim 1, wherein the debranching enzyme is an isoamylase, a pullulanase or a limit dextrinase.

* * * * *